United States Patent [19]

Trofast et al.

[11] Patent Number: 5,562,923
[45] Date of Patent: Oct. 8, 1996

[54] PROCESS FOR CONDITIONING OF WATER-SOLUBLE SUBSTANCES

[75] Inventors: Jan W. Trofast; Eva A. Trofast, both of Lund; Edib Jakupovic, Nykvarn; Katarina U. Byström, Genarp, all of Sweden

[73] Assignee: Aktiebolaget Astra, Sodertalje, Sweden

[21] Appl. No.: 479,494

[22] Filed: Jun. 7, 1995

Related U.S. Application Data

[63] Continuation of Ser. No. 129,204, Oct. 25, 1993, abandoned.

[30] Foreign Application Priority Data

Apr. 11, 1991 [SE] Sweden .................. 9101090
Mar. 24, 1992 [WO] WIPO ............. PCT/SE92/00186

[51] Int. Cl.$^6$ .......................................... A61K 9/14
[52] U.S. Cl. ................ 424/489; 424/488; 424/490
[58] Field of Search ............................ 424/489, 490, 424/491

[56] References Cited

U.S. PATENT DOCUMENTS

| | | | |
|---|---|---|---|
| 3,978,192 | 10/1976 | Wright | 514/522 |
| 4,405,598 | 9/1983 | Brown | 424/45 |
| 4,476,130 | 10/1984 | Wade | 424/267 |

*Primary Examiner*—Thurman K. Page
*Assistant Examiner*—William E. Benston, Jr.
*Attorney, Agent, or Firm*—White & Case

[57] ABSTRACT

A process for providing water-soluble micronized pharmaceutically acceptable inhalable substances, which can be produced, stored and used while maintaining the aerodynamic properties required for inhalation of the pharmaceutically acceptable substances. This process is carried out by the steps of reducing, if necessary, the residual water from the micronized substance by drying at an elevated temperature and/or vacuum; conditioning the dried, micronized pharmaceutically acceptable inhalable substances with a solvent; and eliminating residual solvent by storing under dry conditions as, e.g., in a vacuum or by purging with a dry, inert gas.

14 Claims, No Drawings

PROCESS FOR CONDITIONING OF WATER-SOLUBLE SUBSTANCES

This application is a continuation of application Ser. No. 08/129,204, filed Oct. 25, 1993, now abandoned.

FIELD OF THE INVENTION

The present invention relates to a process for providing water-soluble micronized substances, which can be produced, stored and used while maintaining the aerodynamic properties required for inhalation of such substances and which have improved physicochemical properties in the dry state, thereby facilitating the technical handling and significantly increasing the medical value of the substances.

BACKGROUND OF THE INVENTION

During the past few years, there have been frequent demonstrations of the fact that the appropriate selection of the most suitable crystalline modification significantly can influence the clinical results of a given chemical entity. The chemical and physical stability of a solid compound in a particular dosage form can be modified by presenting the substance in the appropriate crystal form. Little information is available on the role of polymorphism and crystal habit in solid dosage form and powder technology. It is, however, apparent that the appropriate selection of the most suitable crystalline modification, whether arising from polymorphic differences or as a result of solvate complex formation of beth water-soluble substances and less water-soluble substances, such as theophylline, often significantly can increase the medical value of a given drug in a particular dosage form. There are only a few statements available to predict the outcome of a crystallization procedure if e.g. the substance could be involved in different polymorphic or pseudopolymorphic forms. Solid-state transformations may also occur during mechanical treatment, e.g. micronization and by pressure during tableting. While a few generalizations can be made concerning the influence of structural modifications on the tendency of a chosen compound to exhibit polymorphism or other phenomena, a complete understanding of this problem awaits further research. Often "trial and error" approaches are used to develop a successful formulation of a drug. It is necessary to establish the conditions whereby different forms of a substance might be converted to a single form thus eliminating differences in solid-state properties and subsequent different physicochemical properties.

E. Shefter and T. Higuchi have measured the relative rates of dissolution of several crystalline solvated and non-solvated forms of important pharmaceuticals, J. Pharm. Sci., 52 (8), (1963), 781–91.

L. van Campen, G. Zografi and J. T. Carstensen give in a review article an approach to the evaluation of hygroscopicity for pharmaceutical solids, Int. J. Pharmceut. 5, (1980), 1–18.

C. Ahlneck and G. Zografi describe the molecular basis of moisture on the physical and chemical stability of drugs in the solid state, Int. J. Pharmceut., 62, (1990), 87–95.

M. Otsuka et al. have calculated hydration data using various solid-state kinetic models for theophylline anhydrate powder, J. Pharm. Pharmacol., 42, (1990), 606–610.

Hak-Kim Chan and Igor Gonda have examined the properties of respirable crystals of cromoglycic acid by using different methods, J. Pharm. Sci., 78 (2), (1989), 176–80.

A more comprehensive discussion of factors relating to pharmaceutical preformulations and the physicochemical properties of drug substances is given by J. I. Wells in Pharmaceutical Preformulation: The Physicochemical Properties of Drug Substances, John Wiley & Sons, New York (1988). See particularly the chapter about polymorphism pp 86–91.

BRIEF DESCRIPTION OF THE INVENTION

The object of the invention is to provide a process for water-soluble micronized substances, which can be produced, stored and used while maintaining the aerodynamic properties required for inhalation of such substances, by reducing the residual water from the micronized substances, conditioning said dried, micronized substances with a solvent and finally eliminating residual solvent from the substances.

DETAILED DESCRIPTION OF THE INVENTION

The object of the present invention is to provide a reliable process, where the desired polymorphic form can be conveniently and reproducibly prepared. The invention relates to a three step procedure:

a. reducing, if necessary, the residual water from the micronized substance by drying optionally at an elevated temperature and/or vacuum.

b. conditioning said dried micronized substance with a solvent, and c. eliminating the residual solvent by storing the substance in a dry place, such as vacuum, or by purging with an inert gas.

The solvents used in the conditioning step b) are organic alcohols, ketones, esters, acetonitrile and the like, most preferably lower alcohols like methanol, ethanol, n-propanol, isopropanol; lower ketones like acetone, methylethylketone; ethylacetate, preferably in the vapour phase.

According to one preferred embodiment the conditioning step b) is carried out in an inert gas containing solvent vapour.

The inert gas used in step c) and optionally in step b) is preferably nitrogen.

The preferred substances on which the invention is to be applied are carbohydrates, amino acids and drugs.

Carbohydrates, such as lactose, glucose, fructose, galactose, trehalose, sucrose, maltose, xylitol, mannitol, myo-inositol and the like, and amino acids, such as alanine, betaine and the like, are often used as additives in pharmaceutical compositions e.g. as additives in certain inhalation formulations.

Terbutaline sulfate, salbutamol sulfate, fenoterol hydrobromide and bambuterol hydrochloride are highly selective $B_2$-adrenergic agonist having bronchospasmolytic effect and are effective in the treatment of reversible obstructive lung ailments of various genesis, particularly asthmatic conditions. Disodium chromoglycate (DSCG) has been used as a prophylactic agent in the treatment of allergic bronchial asthma for many years.

The invention will be described by using lactose, terbutaline sulfate and salbutamol sulfate as examples. The phenomena of solvate formation and polymorphism are well recognized in the literature in the preformulation studies in the development phase for new drugs in the solid state. e.g. the US Pharmacopoeia recognizes>90 drug hydrates!

Many substances exist in different polymorphs (pseudopolymorphs) and several metastable solvates with variable composition and physical properties like bulk density and hygroscopicity. Several transformations between these polymorphs may occur at different velocity. These effects are operating when crystalline substances have been activated by various processes such as grinding, freeze drying, micronization or recrystallization to produce regions of partial amorphous structure. The substances often will be obtained in an amorphous state or a metastable crystalline form when spray drying, freeze drying, rapid solvent quenching or when using controlled precipitation where beth crystalline and amorphous forms can be prepared. The use of an amorphous form or a metastable crystalline form is often limited due to its thermodynamic instability. It is therefore a desire to convert the amorphous form or the metastable crystalline form to the more stable crystalline state. The present invention deals with such physical and chemical changes, or more importantly, to anticipate them and the means by which these solid-state phenomena can be handled.

After recrystallization (or after spray drying/freeze-drying) the substance has to be micronized to the final particle size required for e.g. inhalation. The particles should be less than 100 μm and preferably less than 10 μm. For crystalline substances, the micronization step seems to give an amorphous outer layer of the particle making the particle more sensitive to moisture.

It is an object of this invention to be able to reliably provide a crystalline form of certain water-soluble substances, which can be produced, stored and used, while maintaining the aerodynamic properties and specifications (particle size, particle form, hygroscopicity etc) required for inhalation of such substances. The particle size of the micronized substances is identical before and after the conditioning step as measured by different instruments like Malvern Master Sizer, coulter counter or a microscope.

The conditioning of the substance probably rearranges the outer layer of the crystals of the amorphous substance giving a more stable and less hygroscopic product.

In some instances it has been possible to use infrared spectroscopy in order to study the conversion of an amorphous form or a partly crystalline form into a stable crystalline form. Other methods available include BET gas adsorption, X-ray powder diffraction, microcalorimetry and differential scanning calorimetry (DSC). We have found that BET gas adsorption and microcalorimetry are the best methods for distinguishing the different forms of the tested compounds.

Test results

The surface area is measured by determining the quantity of a gas (nitrogen) that adsorbs as a single layer of molecules, a monomolecular layer on a sample is formed (Flowsorb II 2300, Micromertics Co, USA). Surface area of the conditions substances were measured after the sample has been standing in high humidity for 24 hrs.

| Micronized substance ($m^2/g$) | Non-conditioned substance ($m^2/g$) | Conditioned substance ($m^2/g$) |
|---|---|---|
| Terbutaline sulfate: | | |
| 11–12.5 | <3 | 7–9 |
| Salbutamol sulfate: | | |
| 8.4 | 3 | 5.9 |

With the low surface area, obtained when non-conditional micronized substance has been stored at high humidity, the bulk substance has a great tendency to aggregate when stored, which makes the substance very difficult for technical handling in manufacturing the different formulations needed.

The interactions between certain substances and water vapour have also been studied by microcalorimetry. When said substances are subjected to water in the vapour phase they give off heat in a highly cooperative process. This moisture induced phase transistion is however not observed for the conditioned substance. Thus, the conditioning process transforms the substance into more stable form that is less sensitive to humidity.

Comparison of the heat given off by non-conditioned and conditioned substances when subjected to water vapour. Experiments are performed by a Thermal Activity Monitor 2277 (Thermometrics, Sweden).

| | Heat (J/g) | |
|---|---|---|
| Relative humidity (%) | Non-conditioned substance | Conditional substance |
| Terbutaline sulfate | | |
| 58 | 3.6 | 0.1 |
| 75 | 6.2 | 0.1 |
| Salbutamol sulfate | | |
| 75 | 6–8 | 0.1 |

When spray-dried lactose has been conditioned in ethanol vapour for 100 hours at room temperature the energy given off was <0.1 J/g, while the unconditioned lactose loses 40–44 J/g when subjected to water vapour.

The stability of the particles being conditioned are astonishing and will in a remarkable way increase the flexibility of the use of the substance for different formulations.

Experimental procedure

The invention is further illustrated but not limited by the following examples.

EXAMPLE 1

3.6 kg terbutaline sulphate micronized was dried in a stainless steel column with 200 mm diameter at 90° C. in vacuum for 23 hours. The dried substance was cooled to abut 30° C. and the pressure was normalized with ethanol-saturated nitrogen gas. 70 ml/min of ethanol-saturated nitrogen gas was then passed through the 200 mm diameter column for 60 hours to condition the substance. During this time the column was inverted a few times. The residual solvent was eliminated by purging with nitrogen gas for 2 hours and the product, about 3.5 kg, was packed in double plastic bags with a drying agent between the bags.

EXAMPLE 2

In one experiment 1 g micronized salbutamol sulfate was kept at room temperature for 24 hours in a closed vessel containing a beaker filled with ethanol. The sample was removed and stored in a completely dry environment over night in order to eliminate traces of ethanol. The sample was subjected for analysis (see test results given above).

It is necessary to introduce stirring or tumbling of the substance when conditioning in larger scale.

EXAMPLE 3

1 g spray-dried amorphous lactose was treated as in example 2. The time kept in the saturated ethanol vapour was 100 hours. After removal of residual ethanol, the sample was subjected for calorimetric analysis (see test results given above).

We claim:

1. A process for preparing a water-soluble micronized active agent or pharmaceutical additive of improved stability, said process comprising:
   a) reducing if necessary the residual water content of the micronized active agent or pharmaceutical additive;
   b) conditioning the dry micronized active agent or pharmaceutical composition with a solvent, and
   c) eliminating residual solvent.

2. The process according to claim 1, wherein, in step a), the residual water content is removed by drying at elevated temperature and/or under vacuum.

3. The process according to claim 1, wherein the solvent used in the conditioning step b) is an alcohol, ketone, ester or acetonitrile.

4. The process according to claim 3, wherein the solvent used in step b) is a lower alcohol, a lower ketone or ethylacetate.

5. The process according to claim 4, wherein the solvent used in step b) is ethanol.

6. The process according to claim 1, wherein the solvent used in the conditioning step b) is in the vapour phase.

7. The process according to claim 1, wherein the conditioning step b) is carried out in an inert gas containing solvent vapour.

8. The process according to claim 1, wherein the conditioning step b) is carried out in the presence of nitrogen.

9. The process according to claim 1, wherein, in step c), the residual solvent is eliminated by storing the micronized active agent or pharmaceutical additive in a dry place or under vacuum, or by purging the micronized active agent or pharmaceutical additive with an inert gas.

10. The process according to claim 1, wherein the residual solvent is eliminated by purging with nitrogen.

11. The process according to claim 1, wherein the pharmaceutical additive is a carbohydrate, glycine, alanine, or betaine.

12. The process according to claim 1, wherein the pharmaceutical additive is selected from the group consisting of lactose, glucose, fructose, galactose, trehalose, sucrose, maltose, xylitol, mannitol, myoinositol, alanine, betaine, glycine and combinations thereof.

13. The process according to claim 1, wherein the active agent is which is an antiasthmatic or antiallergic substance.

14. The process according to claim 1, wherein the active agent is selected from the group consisting of terbutaline sulfate, salbutamol sulfate, fenoterol hydrobromide, bambuterol hydrochloride, terfenadine and disodium cromoglycate.

* * * * *